United States Patent
Courtwright et al.

(10) Patent No.: US 12,364,475 B2
(45) Date of Patent: Jul. 22, 2025

(54) FEATURES TO ENHANCE STAPLE HEIGHT CONSISTENCY IN CURVED SURGICAL STAPLER

(71) Applicant: Cilag GmbH International, Zug (CH)

(72) Inventors: Nicholas D. Courtwright, Villa Hills, KY (US); Jason E. Zerkle, Blanchester, OH (US)

(73) Assignee: CILAG GMBH INTERNATIONAL, Zug (CH)

(*) Notice: Subject to any disclaimer, the term of this patent is extended or adjusted under 35 U.S.C. 154(b) by 86 days.

(21) Appl. No.: 17/752,920

(22) Filed: May 25, 2022

(65) Prior Publication Data

US 2022/0330941 A1    Oct. 20, 2022

Related U.S. Application Data

(63) Continuation of application No. 16/945,042, filed on Jul. 31, 2020, now Pat. No. 11,432,815.

(51) Int. Cl.
*A61B 17/072* (2006.01)
*A61B 17/00* (2006.01)

(52) U.S. Cl.
CPC .. *A61B 17/072* (2013.01); *A61B 2017/00818* (2013.01); *A61B 2017/07221* (2013.01); *A61B 2017/0725* (2013.01); *A61B 2017/07264* (2013.01); *A61B 2017/07271* (2013.01); *A61B 2017/07285* (2013.01)

(58) Field of Classification Search
CPC .......... A61B 17/072; A61B 2017/0725; A61B 2017/07221; A61B 2017/00818; A61B 2017/07264; A61B 2017/07285; A61B 2017/07271; A61B 2017/07242; A61B 2017/07257
USPC ............................................ 227/175.1–182.1
See application file for complete search history.

(56) References Cited

U.S. PATENT DOCUMENTS

| | | | |
|---|---|---|---|
| 5,074,454 A * | 12/1991 | Peters | A61B 17/07207 227/19 |
| 6,988,650 B2 | 1/2006 | Schwemberger et al. | |
| 7,134,587 B2 | 11/2006 | Schwemberger et al. | |
| 7,147,139 B2 | 12/2006 | Schwemberger et al. | |
| 7,147,140 B2 | 12/2006 | Wukusick et al. | |

(Continued)

OTHER PUBLICATIONS

International Search Report and Written Opinion dated Nov. 2, 2021, for International Application No. PCT/IB2021/056957, 15 pages.

*Primary Examiner* — Stephen F. Gerrity
*Assistant Examiner* — Linda J Hodge
(74) *Attorney, Agent, or Firm* — FROST BROWN TODD LLP

(57) ABSTRACT

An apparatus includes a housing, an anvil, a backing member, and a concave surface. The housing has a plurality of staples and the anvil is opposed from the housing such that the anvil and the housing are configured to cooperate to clamp tissue. The anvil is configured to form staples ejected from the housing into the clamped tissue. The backing member is coupled with the anvil and the concave surface defines a gap between the backing member and an adjacent component of the apparatus. The anvil is configured to deflect in a direction towards the gap in response to actuation of the apparatus to at least one of clamp tissue or staple tissue.

20 Claims, 11 Drawing Sheets

(56) References Cited

U.S. PATENT DOCUMENTS

| | | |
|---|---|---|
| 7,204,404 B2 | 4/2007 | Nguyen et al. |
| 7,207,472 B2 | 4/2007 | Wukusick et al. |
| 8,479,969 B2 | 7/2013 | Shelton, IV |
| 8,573,465 B2 | 11/2013 | Shelton, IV |
| 8,800,838 B2 | 8/2014 | Shelton, IV |
| 10,045,780 B2 | 8/2018 | Adams et al. |
| 10,194,913 B2 | 2/2019 | Nalagatla et al. |
| 11,432,815 B2 | 9/2022 | Courtwright et al. |
| 2005/0139634 A1* | 6/2005 | Schwemberger .... A61B 17/072 227/19 |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2007/0167960 A1* | 7/2007 | Roth .................... A61B 17/072 606/153 |
| 2009/0206131 A1* | 8/2009 | Weisenburgh, II ......................... A61B 17/3209 227/180.1 |
| 2011/0278343 A1* | 11/2011 | Knodel ............ A61B 17/07207 227/176.1 |
| 2017/0189024 A1* | 7/2017 | Adams ................ A61B 17/072 |
| 2017/0281173 A1* | 10/2017 | Shelton, IV ......... A61B 17/068 |
| 2017/0367701 A1 | 12/2017 | Park |
| 2019/0247045 A1* | 8/2019 | Park ..................... A61B 17/072 |
| 2020/0029966 A1 | 1/2020 | Zhan et al. |
| 2020/0038018 A1 | 2/2020 | Shelton, IV et al. |
| 2020/0337698 A1 | 10/2020 | Simms |
| 2022/0249090 A1* | 8/2022 | Zhang ................. A61B 17/072 |

\* cited by examiner

FEATURES TO ENHANCE STAPLE HEIGHT CONSISTENCY IN CURVED SURGICAL STAPLER

This application is a continuation of U.S. application Ser. No. 16/945,042, filed Jul. 31, 2020, entitled "Features to Enhance Staple Height Consistency in Curved Surgical Stapler," issued as U.S. Pat. No. 11,432,815 on Sep. 6, 2022.

BACKGROUND

Some surgical staplers are operable to clamp down on one or more layers of patient tissue, form staples through the layers of tissue to substantially seal the layers of tissue together near the formed staples, and cut through the layers of tissue for forming severed ends of operatively sealed tissue. An exemplary stapling instrument may include a pair of cooperating elongate jaw members, where each jaw member may be adapted to be inserted into a patient and positioned relative to tissue that is to be stapled and/or incised. One of the jaw members may support a staple cartridge with at least two laterally spaced rows of staples contained therein, and the other jaw member may support an anvil with staple-forming pockets aligned with the rows of staples in the staple cartridge. Generally, the stapling instrument may further include a pusher bar and a knife blade that are slidable relative to the jaw members to sequentially or simultaneously eject the staples from the staple cartridge via camming surfaces on the pusher bar and/or camming surfaces on a wedge sled that is pushed by the pusher bar. The camming surfaces may be configured to activate one or more staple drivers carried by the cartridge and associated with the staples in order to push the staples against the anvil and form laterally spaced rows of deformed staples in the tissue gripped between the jaw members. Such rows may be arranged as linear rows and/or arcuate rows for sequentially or simultaneously stapling and cutting the tissue of the patient in the form of a predetermined pattern. The knife blade may trail the camming surfaces and cut the tissue along a linear or arcuate line between the rows of staples formed in the tissue.

Merely exemplary surgical staplers are disclosed in U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 14, 2006; U.S. Pat. No. 7,147,139, entitled "Closure Plate Lockout for a Curved Cutter Stapler," issued Dec. 12, 2006, U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007. The disclosure of each of the above-cited U.S. patents is incorporated by reference herein. Additional merely exemplary surgical staplers are disclosed in U.S. Pat. Pub. No. 2005/0139636, entitled "Replaceable Cartridge Module for a Surgical Stapling and Cutting Instrument," published on Jun. 30, 2005, now abandoned; U.S. Pat. Pub. No. 2005/0143759, entitled "Curved Cutter Stapler Shaped for Male Pelvis," published on Jun. 30, 2005, now abandoned; and U.S. Pat. Pub. No. 2005/0145672, entitled "Curved Cutter Stapler with Aligned Tissue Retention Feature," published on Jul. 7, 2005, now abandoned. The disclosure of each of the above-cited U.S. Patent Publications is incorporated by reference herein.

A surgical stapler may be inserted into a patient to perform colorectal surgery. Such procedures may include the use of the stapler to operatively seal, sever, and remove the colon of the patient, in whole or in part. For instance, a proctocolectomy may be performed during a lower anterior resection ("LAR") for treating and inhibiting the spread of colorectal cancer cells. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1A:
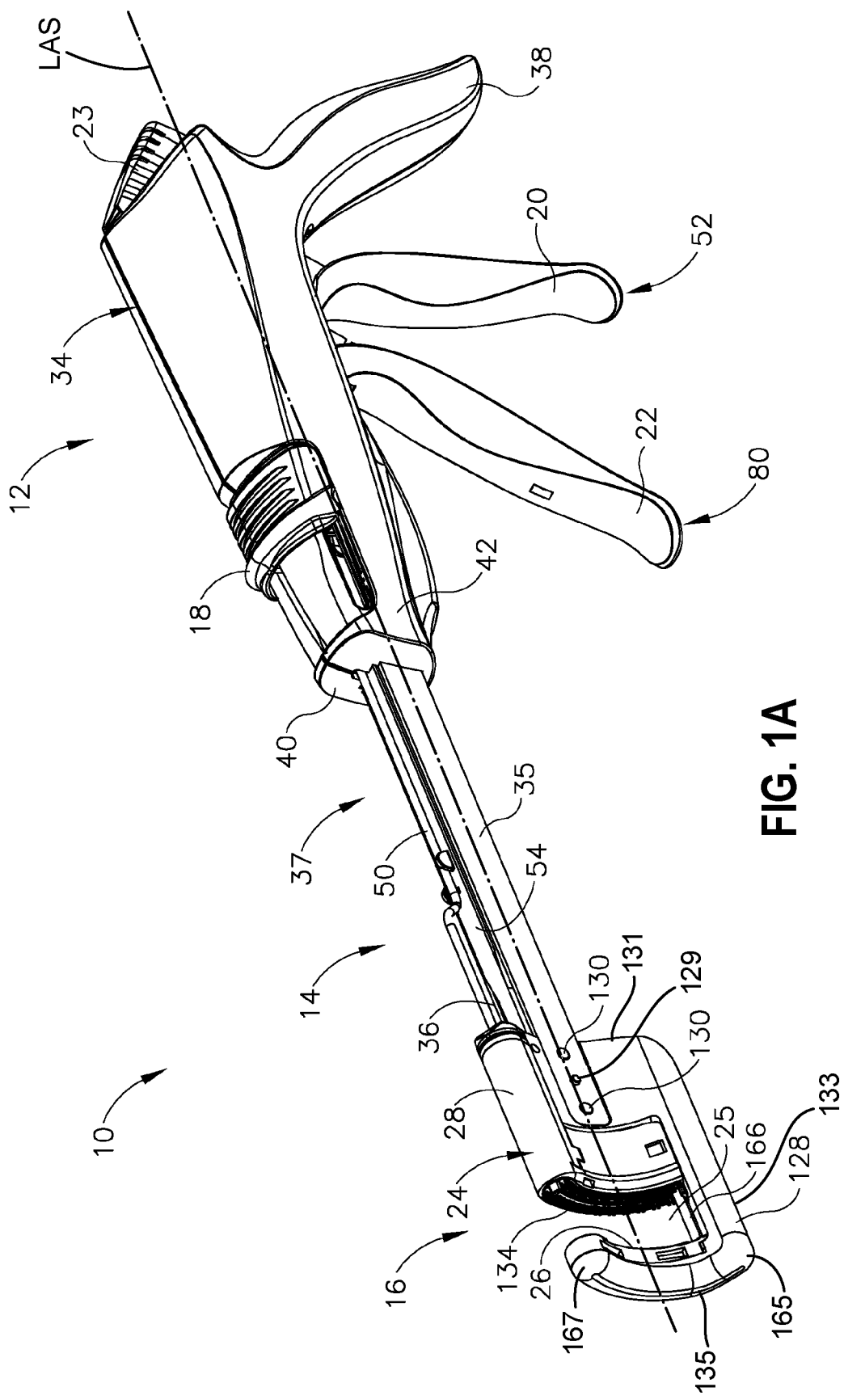
FIG. 1A depicts a perspective view of an exemplary surgical stapling instrument with a pin actuation mechanism in an open position and a staple cartridge unit of an end effector of the instrument in an open position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "vertical," "horizontal," "lower," "upper," "front," and "rear" are used herein with respect to the drawings. However, surgical instruments are used in many orientations and positions, and these terms are not intended to be limiting and/or absolute.

As used herein, the terms "about," "approximately," and the like in connection with any numerical values or ranges of values are intended to encompass the exact value(s) referenced, as well as a suitable dimensional tolerance that enables the referenced feature or combination of features to function for the intended purpose described herein.

I. Overview of Exemplary Surgical Stapler

FIGS. 1A-1D depict an exemplary surgical stapler (10) that includes a handle assembly (12), a shaft assembly (14) extending distally from handle assembly (12), and an end effector (16) at a distal end of shaft assembly (14). It should be understood that terms such as "proximal," "distal," "right," and "left" are used herein with reference to a clinician gripping handle assembly (12) of surgical stapler (10). Thus, end effector (16) is distal with respect to the relatively proximal handle assembly (12). Except as otherwise described herein, surgical stapler (10) may be configured and operable in accordance with at least some of the teachings of U.S. Pat. Pub. No. 2005/0143759, entitled "Curved Cutter Stapler Shaped for Male Pelvis," published on Jun. 30, 2005, now abandoned, the disclosure of which is incorporated by reference herein; and/or U.S. Pat. No. 10,194,913, entitled "Surgical Instrument Comprising Systems for Assuring the Proper Sequential Operation of the Surgical Instrument," issued on Feb. 5, 2019, the disclosure of which is incorporated by reference herein.

Figure 1B:
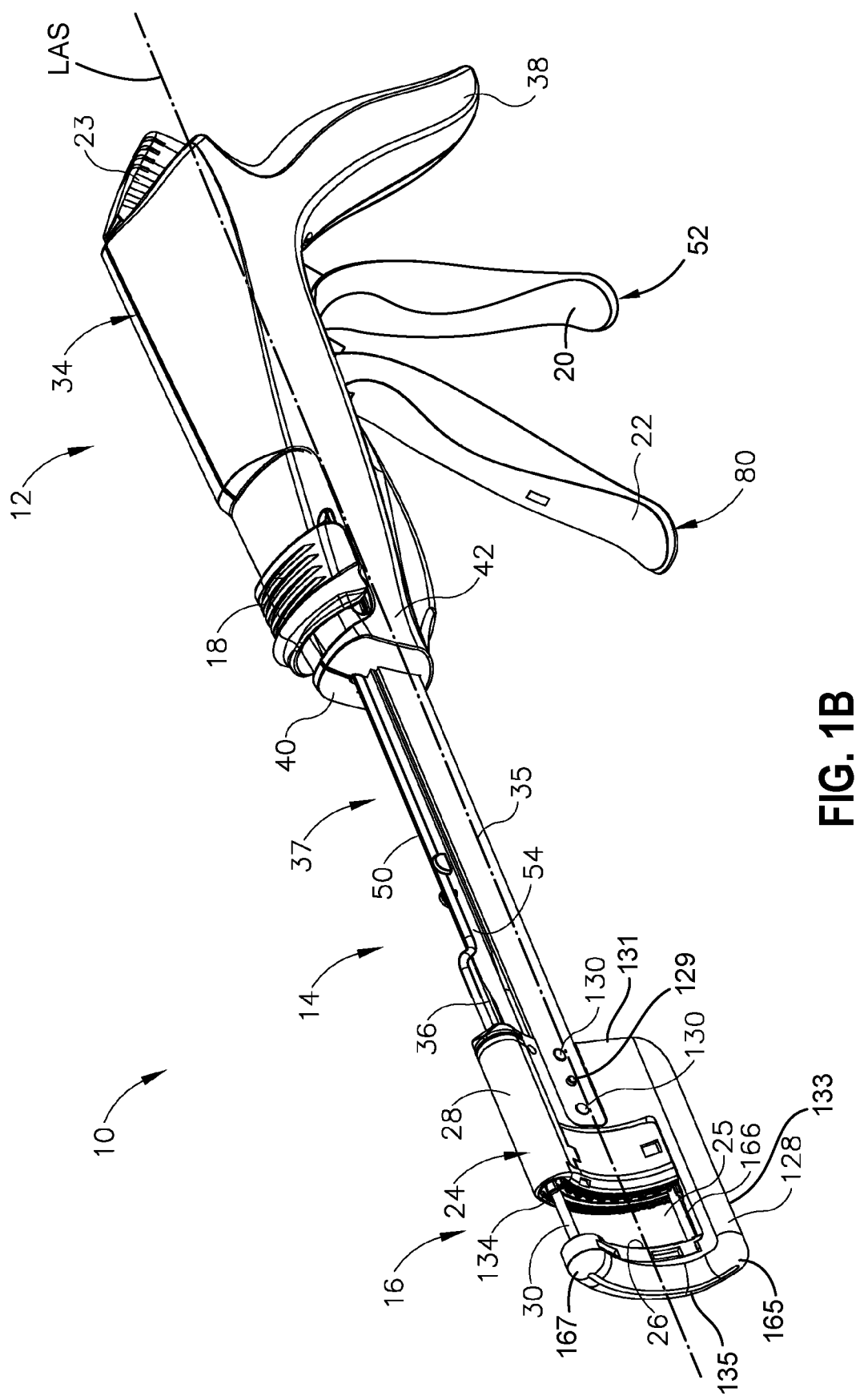
FIG. 1B depicts a perspective view of the surgical stapling instrument of FIG. 1A with the pin actuation mechanism in a closed position and the staple cartridge unit in the open position.
Figure 1C:
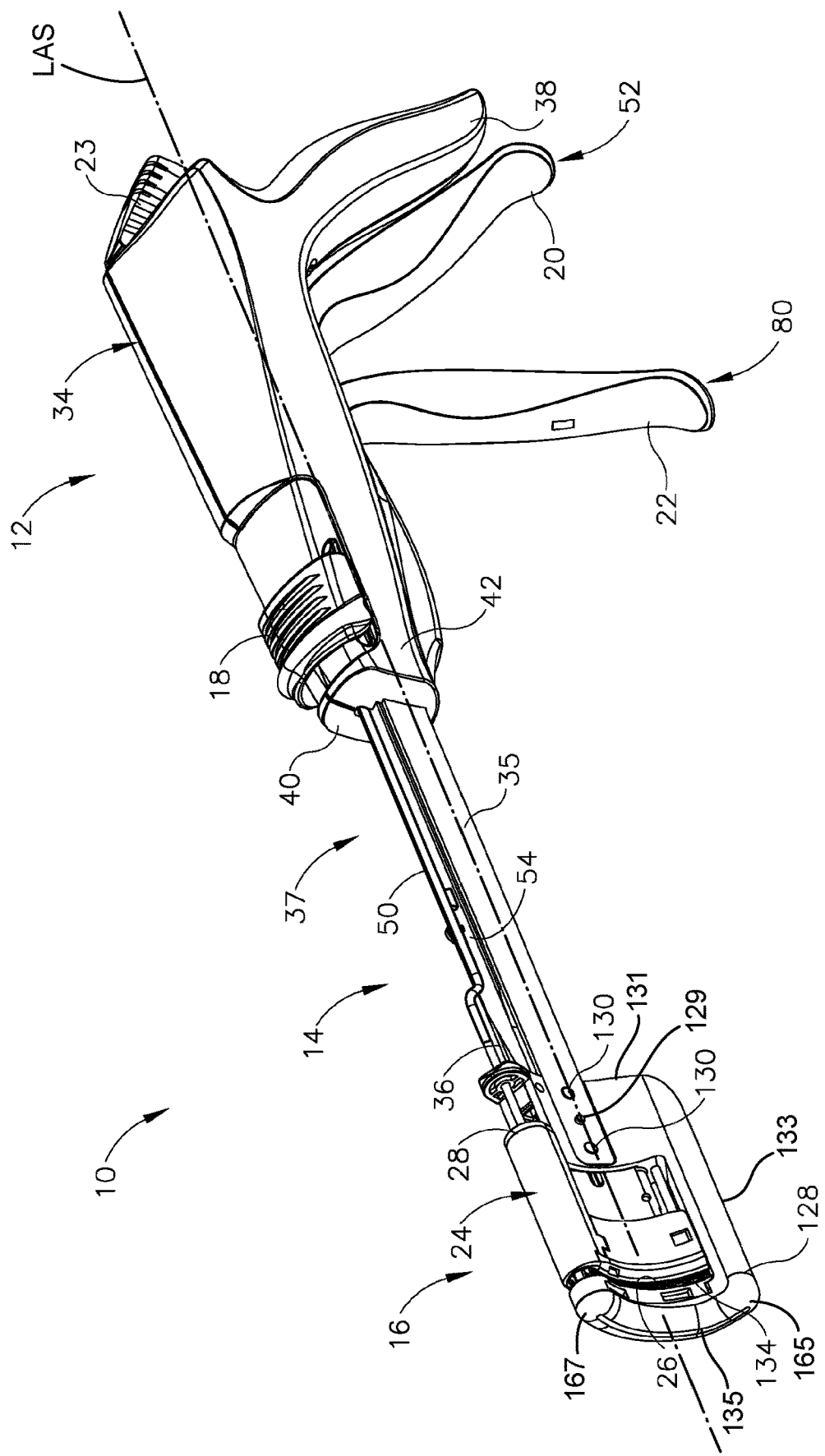
FIG. 1C depicts a perspective view of the surgical stapling instrument of FIG. 1A with the pin actuation mechanism in the closed position and the staple cartridge unit in a closed position via actuation of a closure mechanism.
Figure 1D:
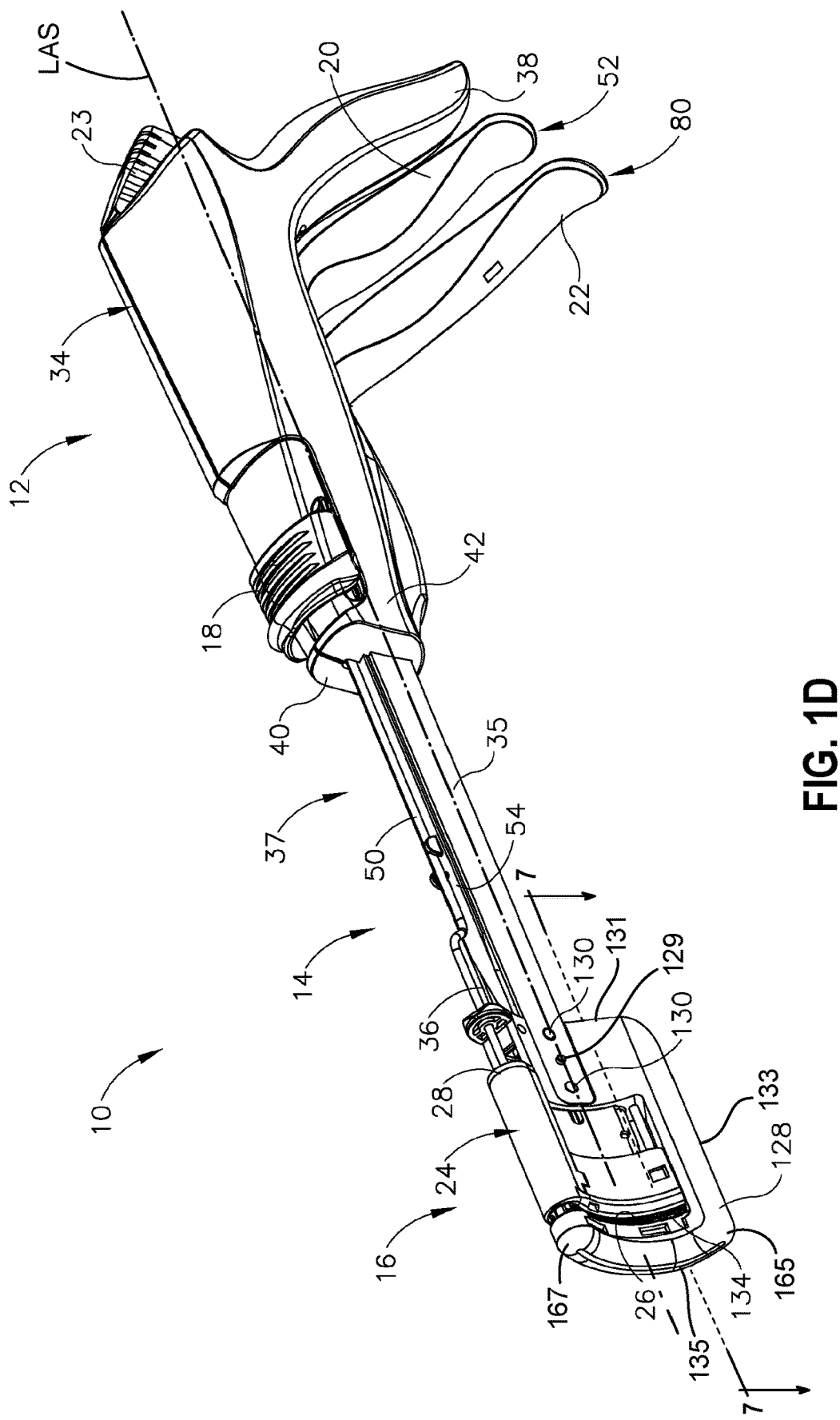
FIG. 1D depicts a perspective view of the surgical stapling instrument of FIG. 1A with the pin actuation mechanism and the staple cartridge unit in the closed positions and a firing trigger in a fired position for stapling and cutting tissue of a patient.

Handle assembly (12) includes several actuation mechanisms for operating end effector (16) during the surgical procedure. To this end, exemplary handle assembly (12) includes a saddle shaped slide (18), a closure trigger (20), and a firing trigger (22) in communication with end effector (16) via shaft assembly (14). FIG. 1A shows slide (18) and closure trigger (20) in open configurations such that end effector (16) is configured to receive tissue laterally within a gap (25) of a replaceable cartridge unit (24) mounted within end effector (16), between an anvil (26) and a cartridge housing (28) of cartridge unit (24). As described in greater detail below, translating slide (18) distally toward end effector (16) slides a retaining pin (30) of end effector (16) distally, as shown in FIG. 1B, for capturing the tissue between anvil (26) and cartridge housing (28). As shown in FIGS. 1C and 1D, sequentially actuating closure trigger (20) and firing trigger (22) respectively compresses the tissue between anvil (26) and cartridge housing (28) in a closed configuration, and then forms a plurality of staples (not shown) within the tissue and severs the tissue with a curved knife (32) (see FIG. 4).

A. Handle Assembly and Shaft Assembly of Surgical Stapler

As shown in FIG. 1A, handle assembly (12) of surgical stapler (10) includes a handle housing (34) and a pair of handle frame plates (35, 36) having proximal portions (not shown) housed within handle housing (34) and elongate distal portions that extend distally along shaft assembly (14). As briefly described above, handle assembly (12) further includes saddle shaped slide (18), closure trigger (20), and firing trigger (22). Handle housing (34) defines a hand grip (38), which the operator may grasp with the palm of at least one hand. Handle housing (34) of the present example is formed by a right shroud handle portion (40) and a left shroud handle portion (42). Closure trigger (20) is proximally positioned relative to firing trigger (22), and each trigger (20, 22) is pivotally mounted to frame plates (35, 36) and are exposed through an underside of handle housing (34) to be manipulated by the fingers of the operator. FIG. 1A shows closure and firing triggers (20, 22) in unactuated positions prior to the closing of end effector (16) and firing of staples (not shown) and curved knife (32). Accordingly, cartridge housing (28) is spaced proximally from anvil (26) for receiving tissue within gap (25) therebetween.

Surgical stapler (10) is operable to capture tissue via a tissue retaining pin actuation mechanism (37) prior to actuation of the closure and firing triggers (20, 22). Tissue retaining pin actuation mechanism (37) includes slide (18)

of handle assembly (12), a tissue retaining pin (30) of end effector (16), and an elongate pushrod (50) of shaft assembly (14). Slide (18) is mounted on an upper surface of handle housing (34) and is configured to linearly translate between proximal and distal positions. Pushrod (50) operatively couples slide (18) with tissue retaining pin (30), such that longitudinal translation of slide (18) drives longitudinal actuation of tissue retaining pin (30) between a proximal open position (see FIG. 1A) and a distal closed position (see FIG. 1B), via pushrod (50).

Figure 2:
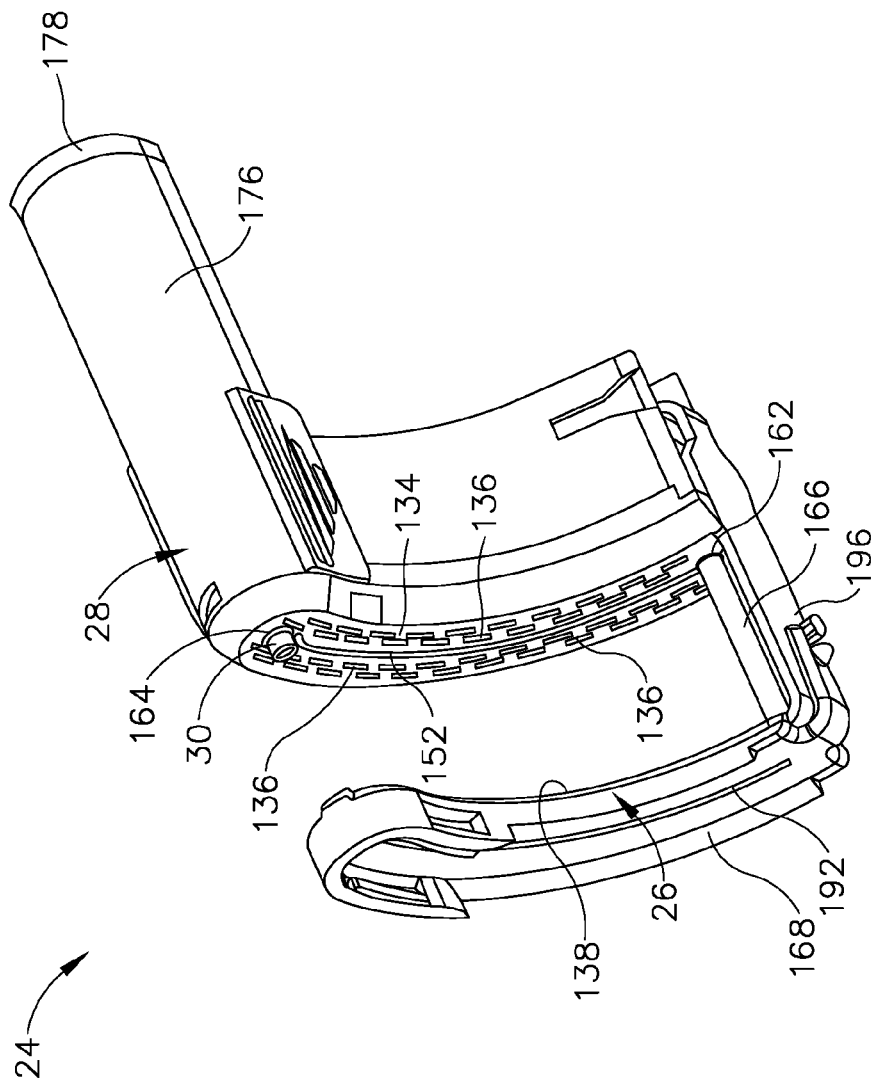
FIG. 2 depicts a distal perspective view of the staple cartridge unit of FIG. 1A.

A closure mechanism (52) of surgical stapler (10) is configured to selectively actuate cartridge housing (28) of cartridge unit (24) between a proximal open position (FIG. 1A) and a distal closed position (FIG. 1C) for clamping tissue between cartridge housing (28) and anvil (26). Closure mechanism (52) includes closure trigger (20) of handle assembly (12) and an elongate closure member (54) coupled at its proximal end with closure trigger (20). Closure member (54) has a generally U-shaped cross-section and extends distally from handle assembly (12), through shaft assembly (14), and into end effector (16), such that a distal end of closure member (54) is configured to receive cartridge unit (24) within end effector (16), as shown in FIG. 2. A proximal end of closure member (54) is operatively connected with closure trigger (20) by a plurality of linkages (not shown) configured to convert pivoting motion of closure trigger (20) into translation of closure member (54). Accordingly, pivoting of closure trigger (20) toward pistol grip (38) to a closed position (FIG. 1C) drives closure member (54) distally, which in turn drives cartridge housing (28) distally toward anvil (26) for clamping tissue therebetween. Subsequently, pivoting of closure trigger (20) away from pistol grip (38) to an open position (FIG. 1A) drives closure member (54) proximally, which in turn drives cartridge housing (28) proximally away from anvil (26) for releasing stapled tissue.

In some versions, closure member (54) may be further configured to cooperate with tissue retaining pin actuation mechanism (37) to automatically actuate retaining pin (30) distally to its closed position when the operator squeezes closure trigger (20). Such automation may be useful in the event that the operator did not manually actuate retaining pin (30) distally via slide (18) prior to squeezing closure trigger (20). Closure trigger (20) may be biased toward the open position by a resilient member (not shown) housed within handle housing (34).

A firing mechanism (80) of surgical stapler (10) is configured to actuate end effector (16) to staple and sever tissue clamped between anvil (26) and cartridge housing (28) in response to manipulation of firing trigger (22) of handle assembly (12). In that regard, firing mechanism (80) includes firing trigger (22), cartridge unit (24), and an elongate firing bar (not shown) that extends longitudinally through shaft assembly (14) and operatively couples firing trigger (22) with cartridge unit (24). Firing trigger (22) is positioned distally of closure trigger (20) such that firing trigger (22) may be pivoted closed only once closure trigger (20) has first been pivoted closed. Pivoting of firing trigger (22) from an open position (FIG. 1C) toward a closed (or "fired") position (FIG. 1D) drives the firing bar distally, which in turn drives internal components of cartridge housing (28) distally to thereby staple and sever the tissue clamped by end effector (16), as described in greater detail below.

One or both of closure trigger (20) and firing trigger (22) may be configured to releasably lock in one or more pivot positions, such as a fully closed position and/or one or more intermediate positions between fully open (i.e., unactuated) and fully closed (i.e., fully actuated), for example. Accordingly, and advantageously, the operator may release one or more hands from the trigger (20, 22) and hand grip (38) to perform another task during the surgical procedure, while the trigger (20, 22) maintains its position. The operator may then release the trigger (20, 22) from its locked state by depressing a release button (23) arranged on a proximal end of handle assembly (12).

Though not shown, shaft assembly (14) of surgical stapler (10) may include various additional components, such as an articulating joint, or may include a rearrangement of various components such that shaft assembly (14) may be modular relative to handle assembly (12).

B. End Effector of Surgical Stapler

As shown best in FIGS. 1A-4, end effector (16) of the present example includes a C-shaped support structure (128) and replaceable cartridge unit (24) removably received by C-shaped support structure (128). The support structure (128) includes a proximal base portion (131), a medial arm (133) that extends distally from proximal base portion (131), and a distal arm (135) that projects laterally (e.g., upwardly) from a distal end of medial arm (133). Proximal base portion (131) is secured to the distal end of handle frame plates (35, 36) at the distal end of shaft assembly (14) by a shoulder rivet (129) and a pair of posts (130). Distal arm (135) includes a fixed end (165) secured to medial arm (133), and a free end (167). Proximal base portion (131) is configured to releasably receive and support cartridge housing (28), and distal arm (135) is configured to releasably receive and support anvil (26) and washer (168).

The term "C-shaped" is used herein as reference to the curvature of support structure (128) and cartridge unit (24), each of which has a concave first lateral side and a convex second lateral side opposed from one another. In other words, support structure (128) and each component of cartridge unit (24) extends along a respective arcuate path in a respective plane that is orthogonal to and intersected by the longitudinal shaft axis (LAS). Such a configuration provides enhanced functionality and access to tissue within the patient. By way of example only, the C-shaped construction of support structure (128) and cartridge unit (24) may enable end effector (16) to easily access the lower colon within the pelvic bowl of a patient, for example for performing a lower anterior resection ("LAR") in a proctocolectomy procedure. Accordingly, the term "C-shaped" as used herein should be construed to include a variety of concave shapes that would similarly enhance the functionality of surgical stapling and cutting instruments. In other versions, cartridge unit (24) and support structure (128) may be shaped in various other curved and non-curved manners. For instance, cartridge unit (24) and support structure (128) may be formed shaped with a linear configuration, for example as described in U.S. patent application Ser. No. 16/395,357, entitled "Tissue Cutting Washer for Right Angle Surgical Stapler," filed Apr. 26, 2019, issued as U.S. Pat. No. 11,266,403 on Mar. 8, 2022, the disclosure of which is incorporated by reference herein.

Replaceable cartridge unit (24) includes anvil (26) and cartridge housing (28), movably coupled to one another by a guide pin (166) and an anvil arm (196), as described in greater detail below. A distal end of cartridge housing (28) defines a distally facing staple deck (134) configured to contact tissue. Staple deck (134) includes a plurality of staple openings (136) arranged in staggered formation in a pair of rows on each side of an arcuate knife slot (152). Various other quantities of rows of staple openings (136) may be provided in other versions. Cartridge housing (28) houses a plurality of staples (not shown) configured to be driven distally through staple openings (136) and against anvil (26) to thereby form the staples in patient tissues. Though not shown, cartridge unit (134) may further include a retainer configured to removable couple to staple deck (134) to cover staple openings (136) and knife slot (152) before use of cartridge unit (24), for instance when cartridge unit (24) is stored, and optionally also after use of cartridge unit (24).

Figure 4:
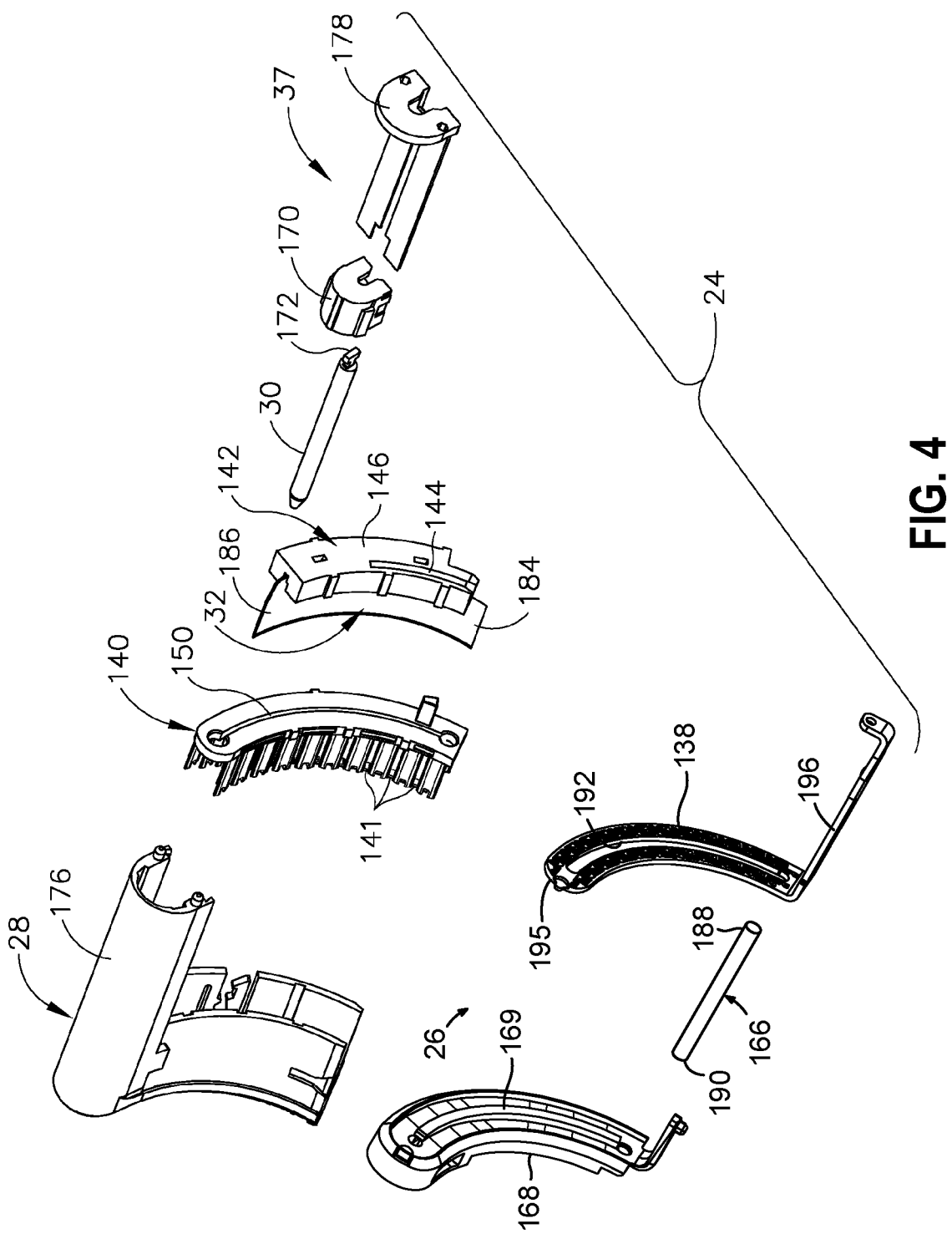
FIG. 4 depicts an exploded perspective view of the staple cartridge unit of FIG. 2.

As shown in FIG. 4, cartridge housing (28) additionally houses retaining pin (30), a staple driver assembly (140), and a knife holder (142). Staple driver assembly (140) is positioned just proximally of the staples (not shown) housed within cartridge housing (28) and distally of knife holder (142). Staple driver assembly (140) of the present example is formed as a unitary structure defining a plurality of staple drivers (141). Thus, the term "assembly," as used in connection with staple driver assembly (140), is not intended to be limited to an assembly of individual components, but may also include integrally formed components with unitary structures. Driver assembly (140) is configured to translate distally within cartridge housing (28) so that staple drivers (141) drive staples distally from respective staple openings (136) and toward anvil (26) for formation within tissue clamped between anvil (26) and cartridge housing (28).

Knife holder (142) is movably disposed within cartridge housing (28) just proximally of staple driver assembly (140). Knife holder (142) supports curved knife (32) along a distal side thereof, and knife holder (142) is configured to translate within cartridge housing (28) such that curved knife (32) extends distally through an arcuate slot (150) of driver assembly (140) and arcuate slot (152) of staple deck (134). A proximal side of knife holder (142) includes a slot (144) and a ledge (146) configured to couple with a knife retractor hook (not shown) for retraction of curved knife (32) after firing of cartridge unit (24), for example as disclosed in U.S. Pat. No. 10,045,780, entitled "Method of Applying Staples in Lower Anterior Bowel Resection," issued Aug. 14, 2018, the disclosure of which is incorporated by reference herein.

As shown in FIG. 2, cartridge housing (28) includes two longitudinally extending, generally circular holes (162, 164) at respective upper and lower ends of arcuate knife slot (152) on staple deck (134). Holes (162, 164) of the present example are positioned such that staple openings (136), and the staples ejected therefrom, extend beyond holes (162, 164) at the upper and lower ends of staple deck (134). Lower hole (162) is shaped and dimensioned to slidably receive a guide pin (166) that extends longitudinally between cartridge housing (28) and anvil (26). Upper hole (164) is shaped and dimensioned to slidably receive retaining pin (30) therethrough, such that retaining pin (30) may actuate longitudinally relative to cartridge housing (28) and anvil (26) between the proximal retracted position (FIG. 1A) and the distal extended position (FIG. 1B).

Figure 3:
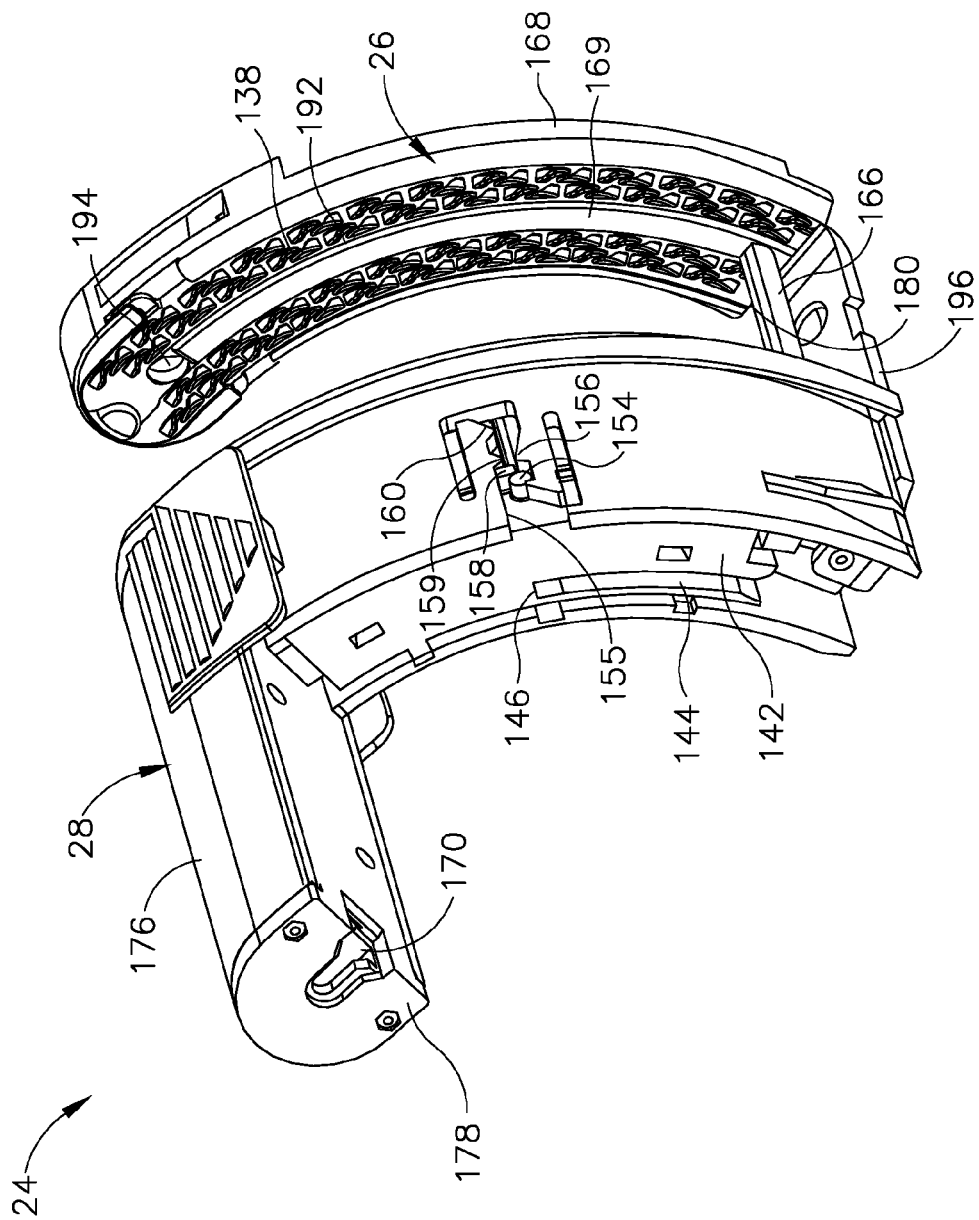
FIG. 3 depicts a proximal perspective view of the staple cartridge unit of FIG. 2.

As shown in FIG. 3, a lateral side of cartridge housing (28) includes a longitudinally extending detent slot (155) defined between a confronting pair of resilient members. A first side of detent slot (155) includes a first proximal detent protrusion (156), and an opposed second side of detent slot (155) includes a second proximal detent protrusion (159) and a distal detent protrusion (160). Detent slot (155) is configured to slidably receive a detent post (154) of knife holder (142) and a detent post (158) of staple driver assembly (140). As staple driver assembly (140) and knife holder (142) translate distally within cartridge housing (28), detent post (154) resiliently engages detent protrusion (156), and detent post (158) resiliently engages detent protrusions (159, 160).

As shown in FIG. 4, a proximal end of retaining pin (30) includes a first coupling feature (172) (e.g., a projection) configured to couple with a corresponding coupling feature (not shown) (e.g., a groove) of a couplet (170), so that retaining pin (30) is secured to couplet (170). Couplet (170) and retaining pin (30) are slidably disposed within an upper arm (176) of cartridge housing (28), and are captured proximally therein by an end cap (178) secured to upper arm (176) proximally of couplet (170). A distal end of pushrod (50) of tissue retaining pin actuation mechanism (37), described above, is operatively coupled with couplet (170). Accordingly, longitudinal actuation of pushrod (50) via slide (18) of handle assembly (12) drives couplet (170) and thus retaining pin (30) longitudinally relative to cartridge housing (28) for capturing tissue to be stapled by end effector (16).

Anvil (26) of the present example includes a plate portion (138), which is secured to a proximal side of an anvil plate backing member (also referred to as a "backing structure") in the form of a plastic cutting washer (168). Anvil plate portion (138) includes an elongate arcuate slot (192) configured to receive a cutting feature of cutting washer (168) in the form of an arcuate projection (169) therethrough to anvil plate portion (138) relative to cutting washer (168). As shown best in FIG. 3, anvil plate portion (138) further includes a plurality of pockets arranged in rows along either side of arcuate slot (192). These pockets are configured to receive and form the legs of staples (not shown) driven distally from staple openings (136) of staple deck (134). Accordingly, anvil (26) is spaced distally from and is aligned with staple deck (134) such that each pocket of anvil plate portion (138) aligns with a respective staple opening (136).

Anvil plate portion (138) further includes a first circular opening (194) disposed at an upper end of arcuate slot (192), and a second circular opening (see FIG. 4) disposed at a lower end of arcuate slot (192). First opening (194) is configured to slidably receive a pointed distal tip of tissue retaining pin (30) when tissue retaining pin (30) is actuated distally to capture tissue positioned between anvil (26) and cartridge housing (28). The lower second opening of anvil plate portion (138) receives a distal end (190) of guide pin (166) therethrough, which extends into and fixedly couples to a lower end of cutting washer (168), such that guide pin (166) is longitudinally fixed relative to anvil (26).

A proximal end (188) of guide pin (166) is slidably received through lower hole (162) formed in staple deck (134) of cartridge housing (28), as described above. An anvil arm (196) projecting proximally from a lower end of anvil plate portion (138) is movably received through an open lower end of cartridge housing (28) to thereby trap proximal end (188) of guide pin (166) within cartridge housing (28), while still permitting cartridge housing (28) to actuate toward anvil (26). Accordingly, cartridge housing (28) is configured to slide longitudinally along guide pin (166) (and tissue retaining pin (30)) relative to anvil (26) in response to actuation of closure trigger (20), described above. As shown in FIG. 4, an interior side of guide pin (166) includes a longitudinal slot (180) configured to slidably receive a corresponding lower end (184) of curved knife (32) as cartridge housing (28) actuates longitudinally relative to anvil (26). An interior side of tissue retaining pin (30) may include a similar longitudinal slot (not shown) configured to slidably receive a corresponding upper end (186) of curved knife (32) as cartridge housing (28) actuates longitudinally relative to anvil (26).

C. Exemplary Actuation of Surgical Stapler

Having described various structural features of surgical stapler (10) above, including cartridge unit (24), exemplary actuation of surgical stapler (10) during a surgical procedure will now be described below. Surgical stapler (10) is first suitably manipulated within a body cavity of a patient to position patient tissue within gap (25) (see FIG. 1A) between anvil (26) and cartridge housing (28). As shown in FIG. 1B, slide (18) is then actuated distally to drive pushrod (50) distally, thereby driving tissue retaining pin (30) distally from cartridge housing (28) toward anvil (26). The pointed distal tip of tissue retaining pin (30) securely engages (e.g., pierces) the tissue and thereby captures the tissue within gap (25).

As shown in FIG. 1C, closure trigger (20) is then squeezed toward pistol grip (38) to drive closure member (54) distally, thereby driving cartridge housing (28) distally toward anvil (26) along tissue retaining pin (30) and guide pin (166) to clamp the tissue between cartridge deck (134) and anvil (26). Cartridge housing (28) may be maintained in this closed position relative to anvil (26) by an internal locking mechanism (not shown) of handle assembly (12) that holds closure trigger (20) in the squeezed position, as described above. As shown in FIG. 1D, while cartridge unit (24) remains in this closed position, firing trigger (22) is then squeezed toward closure trigger (20) and pistol grip (38) to drive the elongate firing bar (not shown) distally, thereby driving staple driver assembly (140) and knife holder (142) distally within cartridge housing (28). Stapler drivers (141) of driver assembly (140) drive staples (not shown) distally through the captured tissue and against anvil plate portion (138) of anvil (26) to form the staples within the tissue and thereby fluidly seal the tissue. As the staples are being formed, curved knife (32) is driven distally by knife holder (142) through arcuate slots (150, 152), through the clamped tissue, and against arcuate projection (169) (see FIG. 5) of cutting washer (168), thereby severing the clamped tissue along an arcuate path (AP) extending between the two innermost rows of the formed staples. Upon cutting fully through the clamped tissue, curved knife (32) may penetrate distally into the arcuate projection (169) of cutting washer (168). Optionally, in response to such penetration, a body of cutting washer (168) may fracture along the distal cutting edge of curved knife (32), thereby providing an audible indication (e.g., via a "snapping" sound) to the surgeon that the firing stroke is complete and that the clamped tissue has been fully stapled and severed.

Similar to closure trigger (20), firing trigger (22) may be held in its squeezed position by the internal locking mechanism (not shown) of handle assembly (12). It will be appreciated that surgical stapler (10) may be configured in some versions such that the tissue clamped by end effector (16) within gap (25) is stapled and cut simultaneously; and be alternatively configured in other versions such that the tissue is fully stapled and subsequently cut in sequential steps.

Once surgical stapler (10) has been fully fired into the patient tissue as described above, the operator may depress release button (23) of handle assembly (12) to release firing trigger (22) and closure trigger (20) from their squeezed positions. In this manner, curved knife (32) may be retracted proximally back into cartridge housing (28), and cartridge housing (28) may be retracted proximally along pins (20, 166) to thereby release the newly stapled and severed tissue from between anvil (26) and cartridge deck (134). The fired cartridge unit (24) may then be removed from support structure (128) of end effector (16), discarded, and replaced for further treatment if so desired.

Surgical stapler (10) may be further configured and operable in accordance with any of the teachings of the references cited herein.

II. Exemplary End Effector with a Concave Surface that Permits Deflection to Enhance Staple Height Consistency As described above, support structure (128) supports and provides rigidity to cartridge unit (24) to define end effector (16). However, in some instances, the free end (167) of support structure distal arm (135) may pivotally deflect in a distal direction about the attached end (165), similar to a cantilever, in response to distally-directed tissue compression and firing forces exerted by cartridge housing (28) and knife (32). In such instances, the staples may be formed with a proper height (i.e., in a distal direction) at the attached end (165) because the attached end (165) does not deflect distally. However, staples may be formed with increasingly greater staple heights in a direction toward free end (167) due to the distal deflection of free end (167) relative to fixed end (165). Accordingly, the resulting heights of formed staples along the arcuate length of staple deck (134) and anvil plate portion (138) may be relatively non-uniform, particularly in instances when tissue thickness varies along this arcuate length. The larger-height formed staples in the region of free end (167) may be incapable of proving effective hemostasis in the corresponding region of tissue.

In addition to or in place of such distal cantilever deflection of free end (167) of distal arm (135), a portion of distal arm (135) inward of free end (167) (i.e., in a direction toward attached end (165)) may deflect proximally in response to closure and/or firing of end effector (16). In some instances, such proximal deflection may be a result of three-point bending effects resulting from the interaction between tissue gap setting protrusions disposed at the inner and/or outer ends of washer (168) and/or anvil plate portion (138), and at the inner and/or outer ends of staple deck (134). Such proximal deflection of a portion of distal arm (135) may also undesirably result in non-uniformity of formed staple heights.

Accordingly, it may be desirable to provide end effector (16) with one or more features that mitigate or otherwise compensate for this deflection of support structure distal arm (135) and thereby promote formation of staples with a uniform staple height along the arcuate length of end effector (16). As described in greater detail below, end effector (16) may include a recess that is defined by a concave surface of the end effector (16). This recess allows a portion of the anvil (26) and/or cutting washer (168) to distally deflect relative to adjacent components of end effector (16) when stapler (10) is fired. Such a configuration may mitigate and compensate for deflection of distal arm (135) to thereby minimize variations in staple height across the arcuate length of the staple deck (134) and anvil plate portion (138), thus providing improved hemostasis by the formed staples.

A. Cutting Washer with Concave Proximal Side

Figure 5:
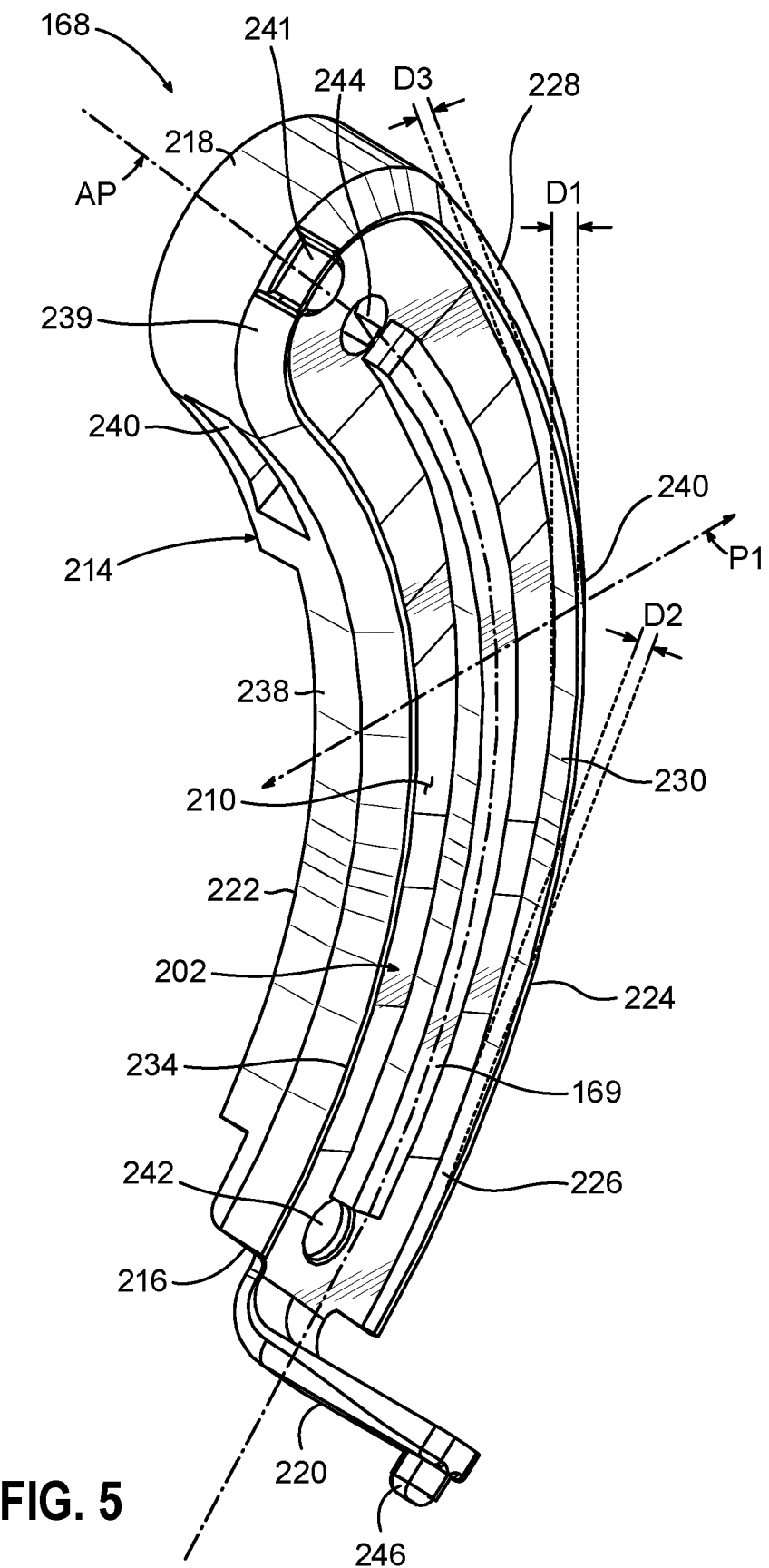
FIG. 5 depicts a proximal perspective view of an exemplary cutting washer of the staple cartridge unit of FIG. 2.

FIG. 5 shows an exemplary configuration in which cutting washer (168) includes a concave proximal surface (210) that allows the anvil plate portion (138) to deflect distally relative to cutting washer (168) during firing of the end effector (16), thereby creating more uniform staple heights. Cutting washer (168) is distally positioned relative to the anvil plate portion (138) and proximally positioned relative to the support structure (128), as shown in FIGS. 2-4. The cutting washer (168) includes a body (214) that transversely extends relative to the shaft longitudinal axis (LAS) (see FIG. 1A-1D) from a first end (216) to a second end (218), and a tang (220) that extends proximally from the first end (216). The body (214) may be C-shaped, J-shaped, or straight, for example. In the present example, the body (214) extends along an arcuate path (AP) in a plane that is orthogonal to and intersected by the shaft longitudinal axis (LAS), and is C-shaped. The curved body (214) includes a distal side (222) that confronts distal arm (135) of support structure (128), and a proximal side (224) that confronts and supports the anvil plate portion (138).

The proximal side (224) of cutting washer body (214) includes a first end portion (226), a second end portion (228), and a middle portion (230). The first end portion (226) extends from the first end (216) toward the middle portion (230), and the middle portion (230) further extends toward the second end portion (228). The second end portion (228) extends to the second end (218). The proximal side (224) also includes a recess (202) that is defined by a concave surface (210), a rim (234), and arcuate protrusion (169). The concave surface (210) extends along the curved longitudinal axis of washer body (214) from the first end (216) to the second end (218). The concave surface (210) proximally faces and extends along the arcuate path (AP).

A rim plane (P1) is defined at the proximal most side of the rim (234). The rim (234) is disposed along an outside edge of the concave surface (210) and extends both proximally and distally from the concave surface (210). The distally extending portion of rim (234) is configured to secure the cutting washer (168) relative to the proximal side of the support structure (128). In the present example, the rim (234) extends distally on three sides of the support structure (128), and includes a pair of clips (240) on the distal side (222) of the concave surface (210) that are configured to aid the support structure (128) in retaining the cutting washer (168). In addition to extending distally, the rim (234) proximally extends around the outside edge of the concave surface (210) along a first elongate edge (238), an edge end (239), and the second elongate edge (240) to the rim plane (P1). The edge end (239) of the rim (234) bends in an arcuate path from the first elongate edge (238) to the second elongate edge (240). The edge end (239) also includes an end retainer (241) configured to retain a corresponding end of the anvil plate portion (138).

The arcuate protrusion (169) proximally extends from concave surface (210) toward the rim plane (P1). The arcuate protrusion (169) extends transversely along the arcuate path (AP) generally between the first edge (238) and the second edge (240). In the present example, the arcuate protrusion (169) generally separates the concave surface (210) and recess (202) to create first and second longitudinal portions of recess (202), each of which is disposed between the arcuate protrusion (169) and a respective one of the first and second elongate edges (238, 240). As described above, arcuate protrusion (169) is configured to be received by the arcuate knife slot (152) of the anvil plate portion (138).

The first end and second end portions (226, 228) of cutting washer body (214) include first and second washer holes (242, 244), respectively, that longitudinally extend through the concave surface (210) and are configured to align with the holes (162, 164), respectively, of cartridge housing (28). The first and second washer holes (242, 244) are configured to align the anvil plate portion (138) with the cutting washer (168) when the first and second washer holes (242, 244) receive guide pin (166) and retaining pin (30), therethrough respectively.

Tang (220) of cutting washer (168) is mated to the first end (216) and extends proximally and follows the contour of the anvil arm (196) as the anvil arm (196) extends proximally. The tang (220) includes a tang bore (not shown) that extends transversely through the tang (220) and a tang nub (246) that extends transversely opposite the direction the body (214) extends. The tang bore aligns with an anvil arm bore (not shown) on the anvil arm (196) to accept a pin (not shown) therethrough to secure the anvil arm (196) to the tang (220). This locking of the tang (220) to the anvil arm (196) longitudinally secures the anvil plate portion (138) relative to the cutting washer (168). The tang nub (246) extends transversely relative to the longitudinal axis of the shaft and is configured to be received within the support structure (128) to longitudinally locate the cutting washer (168) relative to the support structure (128).

Figure 6:
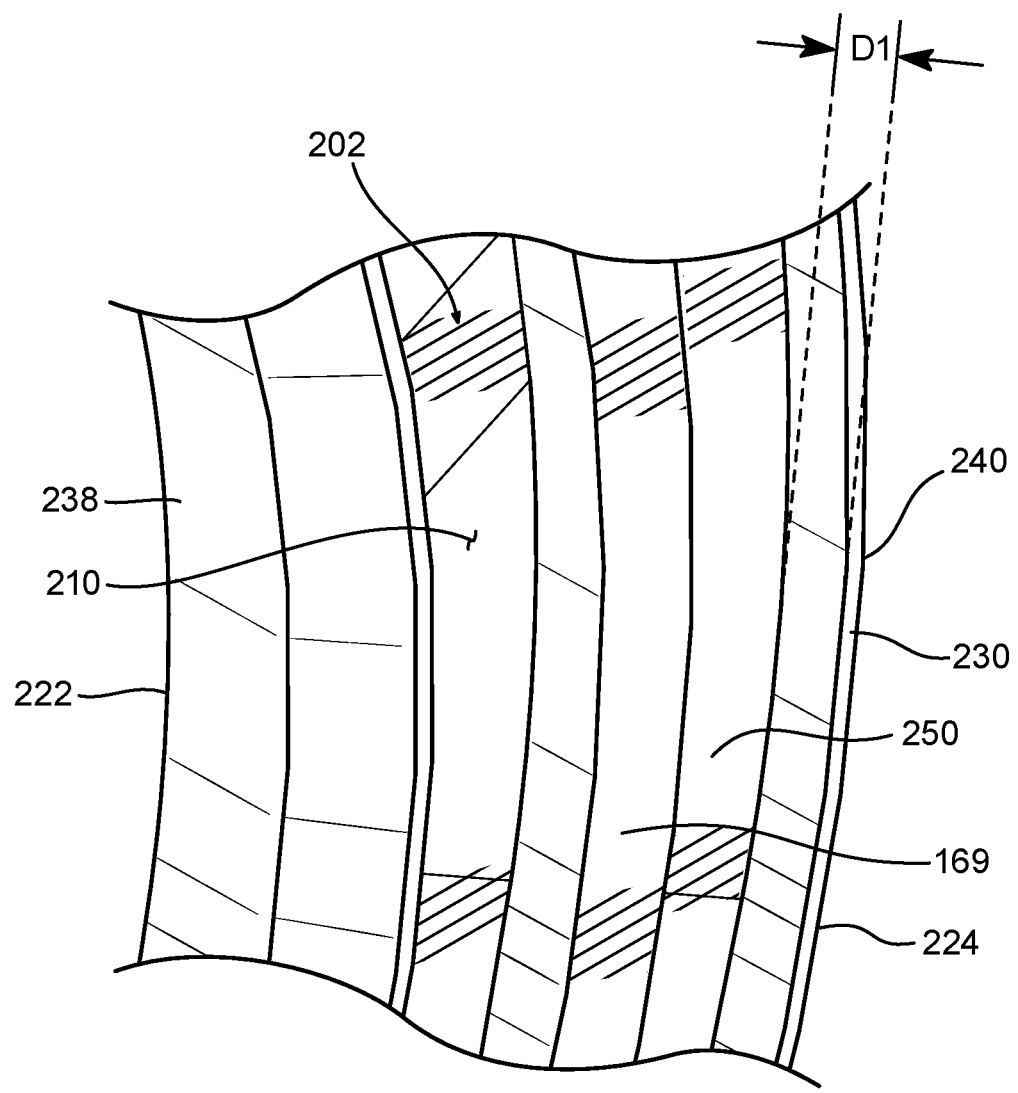
FIG. 6 depicts an enlarged perspective view of a middle portion of the cutting washer of FIG. 5.

As shown best in FIGS. 5-6, concave surface (210) of cutting washer (168) is shaped such that a middle portion depth (D1) of recess (202) in the middle portion (230) of cutting washer body (214) is greater than first and second end depths (D2, D3) of recess (202) in the first and second end portions (226, 228). The depth of recess (202) is defined by the distance, in a proximal-distal direction, from the rim plane (P1) to the concave surface (210). As mentioned above, the rim plane (P1) is defined by the proximal most part of the rim (234) and the proximal most part of the elongate protrusion (169) when the end effector is in a non-deflected state (see FIG. 1A). The first and second end portions (226, 228) of cutting washer body (214) are sized so that the recess (202) accepts the anvil plate portion (138) such that the proximal side of the anvil plate portion (138) generally lies within the rim plane (P1). In some instances, middle portion (230) of concave surface (210) may be formed with a maximum distal depth of approximately 0.005 inches to approximately 0.015 inches relative to first and second end portions (226, 228) of surface (210).

In the present example, the concave surface (210) of cutting washer (168) slopes distally away from the rim plane (P1) as the first end portion (226) extends towards the middle portion (230). In some versions, the curvature of the concave surface (210) may be defined by a single radius that extends around the first end portion (226), through the middle portion (230) to the second end portion (228). In other versions, the curvature of concave surface (210) may be defined by multiple radii. In the middle portion (230), the concave surface (210) continues to slope distally away as the concave surface (210) extends towards the midpoint (250) of the middle portion (230). Once reaching the midpoint (250) of the middle portion (230), the concave surface (210) slopes proximally as it extends towards the second end portion (228). Once reaching the second end portion (228) the concave surface (210) continues to slope proximally until obtaining a depth that generally equals the thickness of anvil plate portion (138) between the rim (234) and the concave surface (210).

In the present version, concave surface (210) is shaped such that first and second end portions (226, 228) are generally planar and lie along a datum plane (not shown) defined by the distal side of the anvil plate portion (138). Additionally, surface (210) may be shaped such that concave middle portion (230) comprises approximately 75% of the arcuate length of surface (210), while first and second planar end portions (226, 228) jointly comprise the remaining 25% of the arcuate length of surface (210). Additionally, relative to a center point along the arcuate length of surface (210), concave middle portion (230) may extend angularly along an arc of approximately 27 degrees in each of a first direction toward first end (216) of washer body (214) and also a second direction toward second end (218) of washer body (214).

The first and second end portions (226, 228) are configured to engage the anvil plate portion (138) in a non-deflected state along the datum plane before stapler (10) is fired. Accordingly, the datum plane acts as a deflection baseline for the deflection of the anvil plate portion (138). The middle portion (230) of concave surface (210) is a distance distal from the first and second end portions (226, 228) and smoothly blends with a curvature into the first and second end portions (226, 228). The concave surface (210) is shaped such that a deepest, distal-most point of middle portion (230) defining recess (202) is centered along the arcuate length of arcuate protrusion (169). In the present version, the first and second end portions (226, 228) engage the anvil plate portion (138) evenly along their lengths as the first and second end portions (226, 228) gradually transition to middle portion (230), which contours smoothly away from the anvil plate portion (138) in the non-deflected state before firing. In some versions, the contour of the middle portion (230) of concave surface (210) may be stepped distally away from the first and second end portions (226, 228).

In the non-deflected state of anvil plate portion (138) (see FIG. 7A), the distal side of a first end of the anvil plate portion (138) rests against the proximal side of the first end (216) of the cutting washer (168), and the distal side of a second end of the anvil plate portion (138) rests against the second end (218) of the cutting washer (168). The distal side of the anvil plate portion (138) and the concave surface (210) define a gap (252) (see FIG. 7A) that is bordered on the sides by the rim (234) and the arcuate protrusion (169) within the recess (202).

Figure 7A:
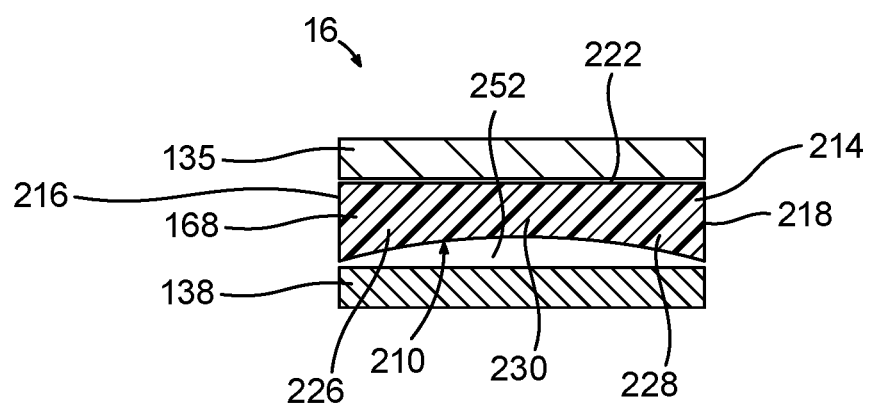
FIG. 7A depicts a schematic sectional view of a portion of the end effector of the surgical stapling instrument of FIG. 1A, taken along line 7-7 of FIG. 1D, showing a concave proximal side of the cutting washer interacting with an anvil of the staple cartridge unit in a non-deflected state.

FIG. 7A schematically shows anvil plate portion (138) in the non-deflected state when end effector (16) is in an open position (see FIG. 1A). A proximal side of the laterally projecting distal arm (135) of support structure (128) is shown abutting distal side (222) of the cutting washer (168). The concave surface (210) is located on the proximal side (224) of the cutting washer (168) as described above and confronts the distal side of anvil plate portion (138) such that first and second ends (216, 218) or first and second end portions (226, 228) of cutting washer body (214) may directly contact and support the first and second ends of the anvil plate portion (138). The gap (252) that is distally rounded lies between the concave surface (210) and the distal side of the anvil plate portion (138). Accordingly, in this non-deflected state of anvil plate portion (138), at least a middle portion of anvil plate portion (138) is spaced proximally from middle portion (230) of cutting washer body (214).

Figure 7B:
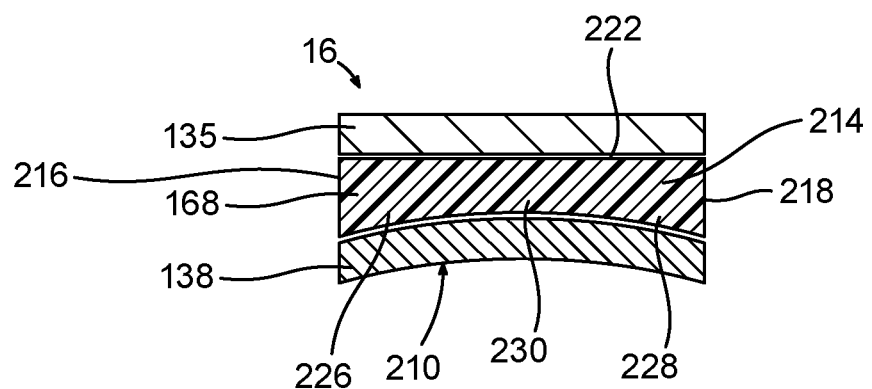
FIG. 7B depicts another schematic sectional view of the end effector portion of FIG. 7A, taken along line 7-7 of FIG. 1D, showing the concave proximal side of the cutting washer tissue interacting with the anvil in a deflected state.

As shown schematically in FIG. 7B, anvil plate portion (138) has transitioned into a distally deflected state relative to cutting washer (168). Such deflection of anvil plate portion (138) may occur in response to actuation of end effector (16) to the closed position (see FIG. 1C) for clamping tissue, and/or upon actuation of end effector (16) to a fired state (see FIG. 1D) in which staples (not shown) and knife (32) have been driven distally through the clamped tissue. The distally-directed staple forming forces and/or tissue compression forces exerted on anvil plate portion (138) cause the middle portion of anvil plate portion (138) to deflect distally into the gap (252) (see FIG. 7A) defined by recess (202) of cutting washer (168) such that the distal side of the anvil plate portion (138) confronts, generally conforms to, and optionally contacts the concave surface (210) of cutting washer (168) from the first end (216) to the second end (218).

This permitted distal deflection of the anvil plate portion (138) into the gap (252) provides an optimized staple forming surface that results in more uniform staple heights across the length of anvil plate portion (138) when stapler (10) is fired. More specifically, the distal deflection of the middle portion of anvil plate portion (138) into the gap (252) may mitigate and/or compensate for cantilevered distal displacement of the free end (167) of support structure distal arm (135) relative to fixed end (165) (see FIGS. 1A-1D) when end effector (16) is closed and fired, as well as any proximal deflection of an inward portion of distal arm (135), by providing a relatively uniform distal spacing between staple deck (134) and anvil plate portion (138) along the arcuate lengths thereof while end effector (16) remains closed on tissue. Uniformity of this distal spacing (also referred to as "tissue gap distance") along the lengths of staple deck (134) and anvil plate portion (138) enables the staples ejected by cartridge housing (28) to be formed by anvil plate portion (138) with relatively uniform heights along the lengths of staple deck (134) and anvil plate portion (138). The resulting uniformity of formed staple heights yields consistent and effective hemostasis along the stapled section of tissue. In some instances, all or a portion of surface (210) of washer (168) may be tapered along its arcuate length to further mitigate the undesirable effects described above caused by the cantilever distal deflection of distal arm (135) during closure and/or firing of end effector (16).

B. Support Structure with Concave Proximal Side

Figure 8:
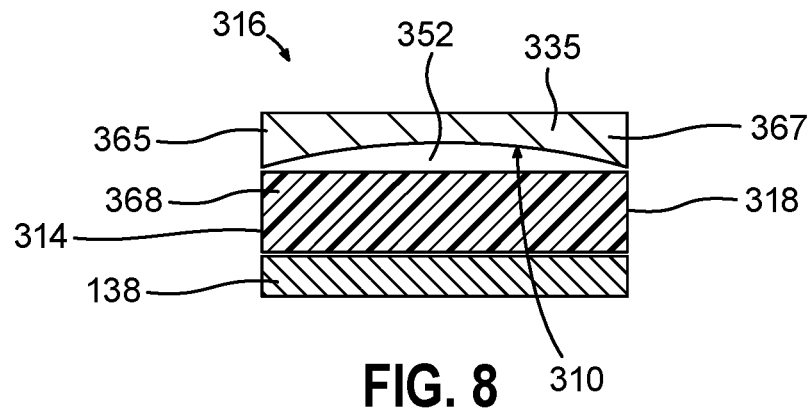
FIG. 8 depicts a schematic sectional view of a portion of another exemplary end effector having a support structure with a concave proximal side, showing the anvil and the cutting washer of the end effector in a non-deflected state relative to the support structure.

In some instances, it may be desirable to substitute or supplement concave proximal surface (210) of cutting washer (168) with a concave surface formed on another portion of end effector (16) to promote uniform staple heights. FIG. 8 shows a portion of another example of an end effector (316) including a concave surface (310) that provides such functional benefits. End effector (316) is constructed and operable similar to end effector (16) described above, except as otherwise described below.

In this example, the concave surface (310) is on the proximal side of the laterally projecting distal arm (335) may be shaped similar to concave surface (210) described above. The end effector (316) is shown in an open position (see FIG. 1A). The concave surface (310) of the laterally projecting distal arm (335) is configured to engage a distal side of the cutting washer (368) at first and second ends (314, 318) and defines a gap (352) that is distally rounded between the concave surface (310) and the distal side of the cutting washer (368). The distal side of the cutting washer (368) defines a datum plane that serves as a plane of engagement along which the first and second ends (314, 318) of the cutting washer (368) engage the laterally projecting distal arm (335) in the non-deflected state. The proximal side of the cutting washer (368) is mated flush with the anvil plate portion (138).

When the end effector (316) transitions to the closed position to clamp tissue (see FIG. 1D) and is subsequently fired to staple and cut the clamped tissue, as detailed above, the staple forming forces and/or tissue compression forces deflect at least the middle portion of the anvil plate portion (138) and the middle portion of the cutting washer (368) in a distal direction and fills the gap (352). During such deflection, the distal side of the cutting washer (368) is configured to mate with the concave surface (310), and the distal side of the anvil plate portion (138) is configured to remain mated to the proximal side of the cutting washer (368) such that anvil plate portion (138) and washer (368) are configured to deflect distally together into the gap (352). The deflection of the cutting washer (368) and the anvil plate portion (138) into the gap (352) may provide a uniform tissue gap distance between staple deck (134) and anvil plate portion (138) along the lengths thereof that compensates for and minimizes distal displacement of free end (367) of support structure distal arm (335) relative to its fixed end (365). This uniformity of tissue gap distance promotes uniform, proper staple heights along end effector (316) that provide effective hemostasis in the stapled tissue.

C. Anvil Plate with Concave Distal Side

Figure 9:
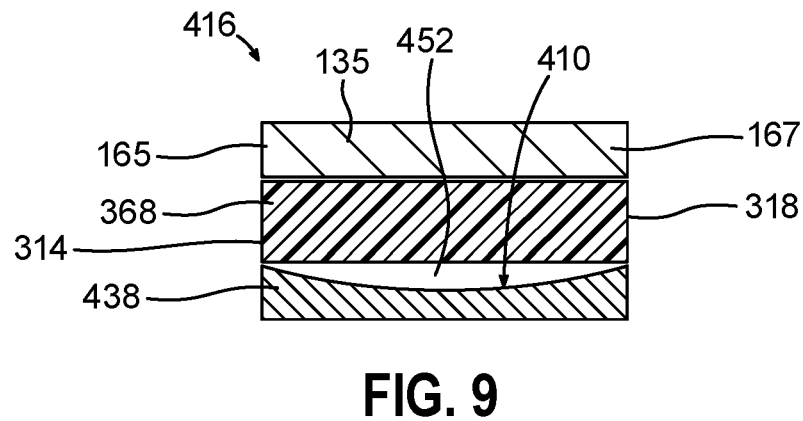
FIG. 9 depicts a schematic sectional view of a portion of yet another exemplary end effector having an anvil with a concave distal side, showing the anvil in a non-deflected state relative to the cutting washer and the support structure.

FIG. 9 shows a portion of yet another example of an end effector (416) including a concave surface (410) that provides similar functional benefits to concave surfaces (210, 310) described above. End effector (416) is similar in construction and function to end effector (16) described above, except as otherwise described below.

In this example, the concave surface (410) is on the distal side of the anvil plate portion (438). The end effector (416) is shown in an open position (see FIG. 1A) and extends from a first end (314) to a second end (318). A distal side of the anvil plate portion (438) includes concave surface (410), which may be shaped similar to concave surface (210) described above. The concave surface (410) engages the proximal side of the cutting washer (368) at the first and second ends (314, 318). The proximal side of the cutting washer (368) defines a datum plane that serves as a plane of engagement along which the first and second ends (314, 318) of the cutting washer (368) engage the anvil plate portion (438) in the non-deflected state. The cutting washer (368) is mated flush with the laterally projecting distal arm (135) of support structure (128). The concave surface (410) and the cutting washer (368) define a gap (452) that is proximally rounded between the first and second ends (314, 318).

When the end effector (416) transitions to the closed position to clamp tissue (see FIG. 1D) and is subsequently fired to staple and cut the clamped tissue as detailed above, the staple forming forces and/or tissue compression forces deflect the middle portion of the anvil plate portion (438) in a distal direction and fills the gap (452). The concave surface (410) of the anvil plate portion (438) is configured to deflect distally and mate with the proximal side of the cutting washer (368) while the distal side of the cutting washer (368) remains mated to the proximal side of the laterally projecting distal arm (135). The deflection of the anvil plate portion (438) into the gap (452) may provide a uniform tissue gap distance between staple deck (134) and anvil plate portion (438) along the lengths thereof that compensates for and minimizes distal displacement of free end (167) of support structure distal arm (135) relative to its fixed end (165). This uniformity of tissue gap distance promotes uniform, proper staple heights along end effector (416) that provide effective hemostasis in the stapled tissue.

D. Cutting Washer with Concave Distal Side

Figure 10:
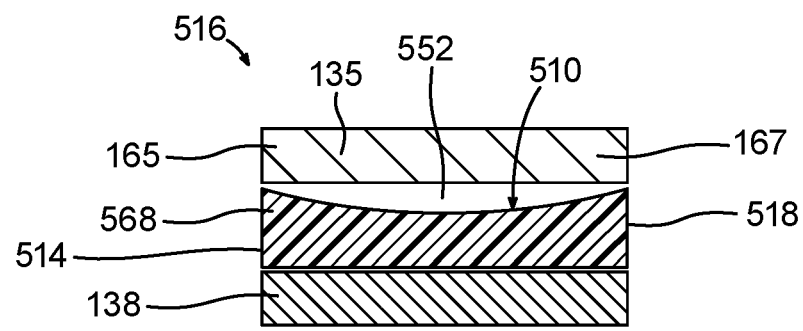
FIG. 10 depicts a schematic sectional view of a portion of yet another exemplary end effector having a cutting washer with a concave distal side, showing the cutting washer and the anvil in a non-deflected state relative to the support structure.

FIG. 10 shows yet another example of an end effector (516) including a concave surface (510) that provides similar functional benefits to concave surfaces (210, 310, 410) described above. End effector (516) is similar in construction and function to end effector (16) described above, except as otherwise described below.

In this example, the concave surface (510) is on the distal side of the cutting washer (568). The end effector (516) is shown in an open position (see FIG. 1A) and extends from a first end (514) to a second end (518). A distal side of the cutting washer (568) includes the concave surface (510), which may be shaped similar to concave surface (210) described above. The proximal side of the laterally projecting distal arm (135) defines a datum plane that serves as a plane of engagement along which the first and second ends (514, 518) of the cutting washer (568) engage the laterally projecting distal arm (135) in the non-deflected state. The proximal side of cutting washer (568) is mated flush with the distal side of the anvil plate portion (138). The concave surface (510) and the laterally projecting distal arm (135) define a gap (552) that is proximally rounded between the first and second ends (514, 518). The proximal side of the cutting washer (568) is mated flush with the anvil plate portion (138).

When the end effector (516) transitions to the closed position to clamp tissue (see FIG. 1D) and is subsequently fired to staple and cut the clamped tissue as detailed above, the staple forming forces and/or tissue compression forces deflect the middle portion of the cutting washer (168) distally into the gap (552). In particular, concave surface (510) of the cutting washer (568) deflects distally and mates with the proximal side of the laterally projecting distal arm (335) while the proximal side of the cutting washer (568) remains mated to the distal side of anvil plate portion (138). Accordingly, in the present version, the middle portions of anvil plate portion (138) and cutting washer (568) are configured to deflect distally together into the gap (552) when end effector (516) is fired. The deflection of the anvil plate portion (138) and washer (568) into the gap (552) may provide a uniform tissue gap distance between staple deck (134) and anvil plate portion (138) along the lengths thereof that compensates for and minimizes distal displacement of free end (167) of support structure distal arm (135) relative to its fixed end (165). This uniformity of tissue gap distance promotes uniform, proper staple heights along end effector (516) that provide effective hemostasis in the stapled tissue.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a housing that includes a plurality of staples; (b) an anvil opposed from the housing, wherein the anvil and the housing are configured to cooperate to clamp tissue, wherein the anvil is configured to form staples ejected from the housing into the clamped tissue; (c) a backing member coupled with the anvil; and (d) a concave surface that defines a gap between the backing member and an adjacent component of the apparatus, wherein the anvil is configured to deflect in a direction towards the gap in response to actuation of the apparatus to at least one of clamp tissue or staple tissue.

Example 2

The apparatus of Example 1, wherein each of the housing, the anvil, and the backing member extends along an arcuate path.

Example 3

The apparatus of any of the preceding Examples, wherein the concave surface is defined by the backing member.

Example 4

The apparatus of any of the preceding Examples, wherein the anvil is arranged distal to the housing, wherein the backing member is arranged distal to the anvil.

Example 5

The apparatus of Example 4, wherein the backing member includes a first end, a second end, and a middle portion therebetween, wherein the concave surface is defined by the backing member such that the backing member includes a concave recess having a maximum depth in the middle portion of the backing member.

Example 6

The apparatus of Example 5, wherein the concave surface is defined on a proximal side of the backing member, wherein the gap is defined between the proximal side of the backing member and a distal side of the anvil, wherein the anvil is configured to deflect into the gap in response to actuation of the apparatus to at least one of clamp tissue or staple tissue.

Example 7

The apparatus of any of the preceding Examples, further comprising a support structure configured to support the backing member, wherein the concave surface is defined by one of the anvil, the backing member, or the support structure.

Example 8

The apparatus of Example 7, wherein the support structure includes a proximal portion and a distal portion, wherein the proximal portion is configured to support the housing, wherein the distal portion is configured to support the anvil and the backing member.

Example 9

The apparatus of any of Examples 7 through 8, wherein the housing is actuatable distally relative to the support structure to clamp tissue against the anvil.

Example 10

The apparatus of Example 1, further comprising a knife movable relative to the housing and the anvil, wherein the knife is configured to cut the clamped tissue.

Example 11

The apparatus of Example 10, wherein the backing member includes a cutting feature configured to cooperate with the knife to cut the clamped tissue.

Example 12

The apparatus of Example 11, wherein the anvil includes an elongate slot, wherein the cutting feature comprises a protrusion that projects through the elongate slot in a direction toward the housing.

Example 13

A surgical instrument comprising: (a) a body; (b) a shaft extending distally from the body; and (c) an end effector at a distal end of the shaft, wherein the end effector includes the apparatus of Example 1.

Example 14

The surgical instrument of Example 13, wherein the end effector includes a support structure that supports the backing member, wherein the concave surface is defined by one of the anvil, the backing member, or the support structure.

Example 15

The surgical instrument of any of Examples 13 through 14, wherein the housing, the anvil, and the backing member collectively define a unit that is removably coupled with the support structure.

Example 16

An apparatus comprising: (a) a body; (b) a shaft extending distally from the body; and (c) an end effector at a distal end of the shaft, wherein the end effector includes: (i) a housing that includes a plurality of staples, (ii) an anvil opposed from the housing, wherein the anvil and the housing are configured to cooperate to clamp tissue, wherein the anvil is configured to form staples ejected from the housing into the clamped tissue, and (iii) a backing member coupled with the anvil, wherein the backing member includes a concave surface that defines a gap between the backing member and an adjacent component of the end effector, wherein the anvil is configured to deflect in a direction toward the concave surface in response to actuation of the apparatus to at least one of clamp tissue or staple tissue.

Example 17

The apparatus of Example 16, wherein the anvil is arranged distal to the housing, wherein the backing member is arranged distal to the anvil, wherein the concave surface is defined by one of a proximal side or a distal side of the backing member.

Example 18

The apparatus of any of Examples 16 through 17, wherein the shaft extends longitudinally along a shaft axis, wherein the housing and the anvil are configured to cooperate to clamp tissue in a plane orthogonal to the shaft axis.

Example 19

An apparatus comprising: (a) a body; (b) a shaft extending distally from the body along a shaft axis; and (c) an end effector at a distal end of the shaft, wherein the end effector includes: (i) a housing that includes a plurality of staples, (ii) an anvil arranged distal to the housing, wherein the anvil and the housing are configured to cooperate to clamp tissue in a plane that intersects the shaft axis, wherein the anvil is configured to form staples ejected from the housing into the clamped tissue, and (iii) a backing member coupled with a distal side of the anvil, wherein a proximal side of the backing member includes a concave surface that defines a gap between the backing member and the distal side of the anvil, wherein the anvil is configured to deflect distally into the gap in response to actuation of the apparatus to at least one of clamp tissue or staple tissue.

Example 20

The apparatus of Example 19, wherein each of the housing, the anvil, and the backing member extends along an arcuate path in a respective plane intersected by the shaft axis.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) a housing that includes a plurality of staples;
(b) an elongate anvil plate opposed from the housing and extending longitudinally between opposed longitudinal end portions, wherein the anvil plate and the housing are configured to cooperate to clamp tissue, wherein the anvil plate is configured to form staples ejected from the housing into the clamped tissue; and
(c) an elongate backing member extending longitudinally between opposed longitudinal end portions, wherein the backing member is coupled with the anvil plate such that the longitudinal end portions of the anvil plate directly abut the longitudinal end portions of the backing member while a longitudinal middle portion of the anvil plate is spaced apart from a longitudinal middle portion of the backing member, wherein the backing member is configured to accommodate deflection of the anvil plate in a direction toward the backing member in response to actuation of the apparatus to at least one of clamp tissue or staple tissue.

2. The apparatus of claim 1, wherein at least the longitudinal middle portion of the backing member is configured to accommodate the deflection of the anvil plate.

3. The apparatus of claim 2, wherein the backing member further includes a concave curved surface, wherein the concave curved surface defines a recess configured to receive the anvil plate when the anvil plate is deflected towards the concave curved surface.

4. The apparatus of claim 3, wherein the concave curved surface is defined by multiple radii.

5. The apparatus of claim 3, wherein the longitudinal middle portion of the backing member comprises approximately 75% of an arcuate length of the concave curved surface.

6. The apparatus of claim 5, wherein the concave curved surface extends angularly along an arc of approximately 27 degrees in each of a first direction towards a first end portion of the opposed longitudinal end portions of the backing member and a second direction towards a second end portion of the opposed longitudinal end portions of the backing member.

7. The apparatus of claim 3, wherein the concave curved surface is defined by at least the longitudinal middle portion of the backing member, wherein the longitudinal middle portion of the backing member is distal to each of the opposed longitudinal end portions of the backing member.

8. The apparatus of claim 3, wherein the concave curved surface is defined by a single radius.

9. The apparatus of claim 1, wherein each of the housing, the anvil plate, and the backing member extends along an arcuate path.

10. The apparatus of claim 9, wherein the backing member further includes an arcuate protrusion that extends along the arcuate path, wherein the backing member is configured to cooperate with a knife member of the apparatus to cut a tissue.

11. The apparatus of claim 10, wherein the anvil plate includes an arcuate slot configured to receive the arcuate protrusion.

12. The apparatus of claim 1, further including a knife member, wherein the backing member is configured to deform and produce an audible sound when the knife member has been fully actuated to cut tissue against the backing member.

13. A surgical instrument comprising:
(a) a body;
(b) a shaft extending distally from the body; and
(c) an end effector at a distal end of the shaft, wherein the end effector includes the apparatus of claim 1.

14. The apparatus of claim 1, wherein the backing member is formed of plastic.

15. The apparatus of claim 1, wherein the longitudinal middle portion of the anvil plate is configured to deflect toward the longitudinal middle portion of the backing member while the longitudinal end portions of the anvil plate remain fixed relative to the longitudinal end portions of the backing member.

16. An apparatus comprising:
(a) a housing that includes a plurality of staples;
(b) an elongate anvil plate opposed from the housing and having a pair of opposed longitudinal end portions, wherein the anvil plate and the housing are configured to cooperate to clamp tissue, wherein the anvil plate is configured to form staples ejected from the housing into the clamped tissue; and
(c) an elongate backing structure coupled with the anvil plate and extending longitudinally between first and second longitudinal ends that directly contact and support the longitudinal end portions of the anvil plate, wherein a longitudinal middle portion of the backing structure includes a concave curved surface that is spaced apart from the anvil plate and extends longitudinally between the first and second longitudinal ends and is configured to permit deflection of a longitudinal middle portion of the anvil plate in a direction toward the backing structure in response to actuation of the apparatus to at least one of clamp tissue or staple tissue.

17. The apparatus of claim 16, wherein the longitudinal middle portion of the anvil plate is configured to deflect toward the longitudinal middle portion of the backing structure while first and second longitudinal ends of the anvil plate remain in flush contact with and stationary relative to the first and second longitudinal ends of the backing structure.

18. The apparatus of claim 16, wherein the housing is actuatable relative to the anvil plate to clamp tissue therebetween.

19. An apparatus comprising:
(a) a housing that includes a plurality of staples;
(b) an elongate anvil plate distal to the housing and having a pair of opposed longitudinal end portions, wherein the anvil plate and the housing are configured to cooperate to clamp tissue, wherein the anvil plate is configured to form staples ejected from the housing into the clamped tissue; and
(c) an elongate backing structure that abuts a distal side of the anvil plate and extends longitudinally between opposed longitudinal end portions that directly contact and support the longitudinal end portions of the anvil plate so as to define a gap between a longitudinal middle portion of the backing structure and a longitudinal middle portion of the anvil plate, wherein in response to actuation of the apparatus to at least one of clamp tissue or staple tissue the backing structure is configured to permit deflection of the longitudinal middle portion of the anvil plate in a distal direction into the gap.

20. The apparatus of claim 19, wherein the longitudinal middle portion of the backing structure includes a concave curved surface facing toward the anvil plate and configured to permit the deflection of the longitudinal middle portion of the anvil plate in the distal direction.

\* \* \* \* \*